United States Patent [19]
Fairbanks et al.

[11] Patent Number: 6,150,419
[45] Date of Patent: Nov. 21, 2000

[54] AGMATINE AS A TREATMENT FOR NEUROPATHIC PAIN

[76] Inventors: Carolyn A. Fairbanks, 620 Colombia Ct., NE., Rochester, Minn. 55906; George L. Wilcox, 2560 Kyle Ave. N., Minneapolis, Minn. 55422; Kristin Schreiber, 12915 N. Thomas Dr., Mequon, Wis. 53097; Tinna Marie Laughlin, 3800 Rum River Dr., Anoka, Minn. 55303

[21] Appl. No.: 09/502,202

[22] Filed: Feb. 10, 2000

Related U.S. Application Data

[63] Continuation of application No. PCT/US98/17033, Aug. 17, 1998.
[60] Provisional application No. 60/055,847, Aug. 15, 1997.

[51] Int. Cl.$^7$ .................................................. A61K 31/155
[52] U.S. Cl. .......................... 514/634; 514/937; 514/866
[58] Field of Search .................................. 514/634, 937, 514/866

[56] References Cited

U.S. PATENT DOCUMENTS

| | | | |
|---|---|---|---|
| 5,352,683 | 10/1994 | Mayer et al. | 514/289 |
| 5,534,495 | 7/1996 | Pert et al. | 514/16 |
| 5,587,454 | 12/1996 | Justice et al. | 530/324 |
| 5,677,349 | 10/1997 | Gilad et al. | 514/634 |

FOREIGN PATENT DOCUMENTS

WO 96/32100  10/1996  WIPO .

OTHER PUBLICATIONS

John J. Bonica, The Management of Pain, Second Edition, vol. 1, pp. 1–17, 1990.
Terence J. Coderre et al., Contribution of central neuroplasticity to pathological pain: review of clinical and experimental evidence, pp 259–285, 1992.
Gad M. Gildad et al., Accumulation of exogenous polyamines in gerbil brain after ischemia, Molecular and Chemical Neuropathology, vol. 18, pp. 197–210, 1993.
Andy Dray et al., Pharmacology of chronic pain, TiPS, vol 15, pp. 190–197, 1994.
Clifford J. Woolf et al., The pathophysiology of chronic pain – increased sensitivity of low threshold Aβ–fiber inputs, Current Opinion in Neurobiology 1994, 4:425–534.
Fernando Cervero et al, From acute to chronic pain: mechanisms and hypotheses, Progress in Brain Research, vol. 110, pp. 3–15, 1996.
Bradley S. Galer, MD, Neuropathic pain of peripheral origin: Advances in pharmacologic treatment, Neurology 45 (Suppl 9), pp. S17–S25, 1995.
Gilbert R. Gonzales, MD., Central Pain: Diagnosis and treatment strategies, Neurology 45 (Suppl 9), pp. S11–S16, 1995.
Anthony H. Dickenson, Central acute pain mechanisms, Annals of Medicine 27:223–227, 1995.
A. Dray et al, New Pharmacological strategies for pain relief, *Annu. Rev. Pharmacol. Toxicol,* pp. 36–253–80, 1996.
Gad M. Gilad et al, Agmatine treatment is neuroprotective in rodent brain injury models, Life Science, vol. 58, No. 2, pp pl 41–46, 1996.
Tinna M. Laughlin et al., Spinally administered dynorphin A produces long–lasting allodynia: involvement of NMDA but not opioid receptors, International Association for the Study of Pain, pp. 253–260, 1997.
Brochure, The UCSF Pain Clinical Research Center (PCRC), 1997.
Brochure, Triggering Mechanism of Neuropathic Pain, 1997.
W.D. Willis et al., Neuroanatomy of the pain system and of teh pathways that modulate pain, *Journal of Clinical Neurophysiology,* vol. 14, No. 1, pp. 2–31, 1997.
Brochure, *Pain Terms,* pp. 210–211, (1997).
Chemical Abstracts, vol. 112, No. 11, issued Mar. 12, 1990, Ralph H. Loring, "Agmatine acts as an antagonist of neuronal nicotinic receptors", p. 145, column 2, abstract no. 92350w, br. J. Pharmacol., 99(1), pp. 207–11, see entire abstract.

*Primary Examiner*—Frederick Krass
*Attorney, Agent, or Firm*—Kinney & Lange, P.A.

[57] ABSTRACT

A treatment and composition for neuropathic pain by administering an effective amount of agmatine.

6 Claims, 4 Drawing Sheets

AGMATINE AS A TREATMENT FOR NEUROPATHIC PAIN

CROSS-REFERENCE TO RELATED APPLICATION(S)

This is a continuing application of International Application PCT//US98/17033, with an international filing date of Aug. 17, 1998, which claims the benefit of U.S. Provisional Application No. 60/055,847, filed Aug. 15, 1997.

STATEMENT OF GOVERNMENT RIGHTS

This invention was made with government support under grants DA01933 and DA04274 from the National Institutes of Health. The government has certain rights in this invention.

BACKGROUND OF THE INVENTION

The present invention relates generally to a treatment for chronic pain in general and neuropathic pain in particular. More particularly, the present invention relates to using agmatine as a treatment for neuropathic pain.

Chronic Pain

A large number of disease states (e.g., cancer, AIDS), inflammatory conditions (e.g., arthritis), metabolic disorders (e.g., diabetes) and injuries (e.g., amputations) can give rise to chronic pain, pain persisting more than a few months; other forms of chronic pain have no known origin and are termed idiopathic. Neuropathic pain, pain deriving from dysfunction of the central or peripheral nervous system, may also be a consequence of damage to peripheral nerves or to regions of the central nervous system, may result from disease or may be idiopathic. The common feature of each of these forms of pain is that a person may endure unrelenting pain that is usually resistant to common forms of analgesic therapy.

Symptoms of neuropathic pain include unusual sensations of burning, tingling, electricity, pins and needles, stiffness, numbness in the extremities, feelings of bodily distortion, allodynia (pain evoked by innocuous stimulation of the skin), and hyperpathia (an exaggerated pain response persisting long after the pain stimuli cease).

Several common causes of neuropathic pain are diabetes, cancer chemotherapy, herpes zoster infection, cervical or lumbar root compression owing to degenerative spine disease, malignant lesions of nerve plexus or root, nerve degeneration, such as from amputation, HIV infection, and lesions of central pain pathways, including spinothalamic tract, thalamus, or thalamic radiations. (Max, 1991).

Additional causes of neuropathic pain include drug-induced, or toxic, neuropathies. For example, anti-virals ddI and ddC commonly cause peripheral neuropathies, as do phenytoin (a seizure medication), isoniazid (a tuberculosis medication), vincristine (a cancer chemotherapeutic agent), high dose vitamins, and folic acid antagonists.

Commonly used analgesics, such as morphine, codeine, tramadol, and aspirin have proven effective by temporarily alleviating neuropathic pain. However, the analgesic effects of these compounds are almost always transient; the vast majority of patients treated with these analgesics; continue to experience pain unless readministered the analgesic.

Both scientific and clinical experience indicate that states of neuropathic pain are difficult to treat chronically with narcotic analgesics (e.g., morphine). Furthermore, both narcotic and some non-narcotic (i.e., clonidine, an alpha-2 adrenergic receptor agonist) analgesics induce contraindicating side effects including constipation (opioid), hypotension (adrenergic), respiratory depression (opioid), pharmacological tolerance (opioid and adrenergic), physical dependence/withdrawal (opioid), sedation (opioid and adrenergic), and dry mouth (adrenergic). These side effect profiles can impact both physician distribution and patient tolerance/acceptance of analgesic therapy using these agents. A number of other substances have also been used with varying degrees of success in the treatment of neuropathic pain. These include the antidepressant amitriptiline, the anticonvulsants carbamazepine, the antiarrythmic drug mexiletine, and the local anesthetics lidocaine and tocaimide; these agents also suffer from limited efficacy or significant side effects. (Dray et al. 1994) The limitations of the current armamentarium of analgesics call for development of non-toxic therapeutics with novel or unidentified mechanisms of action. Along those lines, several patents on such compounds have recently been assigned.

Mayer et al., U.S. Pat. No. 5,352,683, discloses administering non-toxic N-methyl-D-aspartate (NMDA) receptor antagonists, such as dextromethorphan, dextrorphan, or ketamine for the treatment of chronic pain.

Pert et al., U.S. Pat. No. 5,534,495, describes a treatment for non-HIV neuropathic pain by administering an effective amount of a peptide that is capable of blocking the loss, destruction, or dysfunction of the cellular constituents that lead to non-HIV neuropathic pain.

Justice et al., U.S. Pat. No. 5,587,454, discusses the use of omega conopeptides to produce analgesia for certain types of neuropathic pain In which morphine was not expected to produce positive results.

Unlike the prevention by pre-treatment or acute attenuation by post-treatment with the NMDA receptor antagonists (e.g., dextromethorphan, ketamine) described in U.S. Pat. No. 5,352,683, we observe that post-treatment with agmatine produces a chronic and perhaps permanent reversal of pain-related behaviors induced by chemical treatment or spinal nerve ligation.

To assist in the study of neuropathic pain, techniques have been developed to chemically induce allodynia in mice or rats by injection of dynorphin A. (Laughlin et al. 1997 and Vanderah et al. 1996) and mechanically induce allodynia in mice or rats by L5/(L6) spinal nerve ligation. (Kim and Chung 1992; Chung and Chung 1997.)

Agmatine

Agmatine is thought to be an endogenous ligand for the imidazoline receptor (Li. et. al. 1994). In addition, published studies suggest that agmatine also blocks the enzyme neuronal nitric oxide synthase (nNOS) (Galea, 1996) which is selectively found in neurons as well as inducible nitric oxide synthase (iNOS) (Auguet et al. 1995 and Galea et al. 1996), which is induced in immune cells by inflammatory stimuli. Other published studies have found that systemic pre- or co-treatment with agmatine reduces excitotoxin-induced loss of cells in primary cerebellar cultures and animals models of ischemia (Gilad et al. 1996) and Gilad et al., U.S. Pat. No. 5,677,349, describes a treatment for stroke. Although agmatine can antagonize NMDA receptors (Yang and Reis, 1997), we have determined that the doses required for the anti-neuropathic pain therapeutic effect claimed herein is maximum far below the dose necessary for blockade of these receptors. This result suggests that other mechanisms are responsible for the therapeutic effects of agmatine that we claim here.

REFERENCES

Aanonsen, L. M., Wilcox, G. L. (1986) Phencyclidine selectively blocks a spinal action of N-Methyl-D-Aspartate in mice. Neurosci. Lett. 67: 191–197.

M. Auguet et al. (1995) *Selective Inhibition of Inducible Nitric Oxide Synthase by Agmatine,* JAPAN J. PHARMACOLOGY 69, 285.

R. Beitel et al. (1976) *Response of Unmyelinated (C) Polymodal Nocicieptors to Thermal Stimuli Applied to Monkey's Face,* J. NEUROPHYSIOLOGY 39, 1160.

Bradley K J and Headley P M Effect of agmatine on spinal nociceptive reflexes: lack of interaction with alpha2-adrenoceptor or mu-opioid receptor mechanisms. European Journal of Pharmacology. 331(2–3): 133–8, Jul. 23, 1997.

H. Bratzke et al. (1988) *Drug-induced Unconsciousness With Subsequent Criminal Acts,* ARCHIV FUR KRMINOLOGIE 181, 33.

Chung, K., Noh, H. , Chung, J. M. (1996) The development of tactile hypersensitivity varies among strains of the mice after a peripheral nerve injury. Soc. Nsci Abst. 22(2): 864.

D. Corbett (1989) *Possible Abuse Potential of the NMDA Antagonist MK-801,* BEHAVIORAL BRAIN RESEARCH 34, 239.

Dalo, N L and Larson, A A Effects of urethane and ketmaine on substance P- and excitatory amino acid-induced behavior in mice. European Journal of Pharmacology Aug. 2, 1990; 184 (1):173–177.

M. Dillman (1995) *Substance Abuse in the Perioperative Setting,* AORN J. 62, 111.

A. Dray et al. (June 1994) *Pharmacology of Chronic Pain,* TiPS 15, 190.

Fairbanks, C. A. and Wilcox, G. L. Acute tolerance to spinally administered morphine compares mechanistically with chronically induced morphine tolerance. J Pharmacol Exp Ther. 282:1408–1417 (1997).

E. Galea et al. (1996) *Inhibition of Mammalian Nitric Oxide Synthases by Agmatine, an Endogenous Polyamine Formed by Decarboxylation of Arginine,* BIOCHEM J. 316, 247.

G. Gilad et al. (1996) *Agmatine Treatment is Neuroprotective in Rodent Brain Injury Models,* LIFE SCIENCES 58, PL41-6.

R. Johansson et al. (1980) *Thresholds of Mechanosensitive Afferents in the Human Hand as Measured with von Frey Hairs,* BRAIN RESEARCH 184, 343.

Kim, S. H., Chung, J. M. (1992) An experimental model for peripheral neuropathy produced by segmental spinal nerve ligation in the rat. Pain 50(3): 355–63.

Kolesnikov, Y., Jain, S. and Pasternak, G. W. Modulation of opioid analgesia by agmatine. Eur. J. Pharm. 296:17–22 (1996).

R. LaMotte et al. (1986) *Tactile Detection of a Dot on a Smooth Surface: Peripheral Neural Events,* J. NEUROPHYSIOILOGY 56, 1109.

T. Laughlin et al. (1997) *Spinally Administered Dynorphin A Produces Long-Lasting Allodynia: Involvement of NMDA but not Opioid Receptors,* PAIN 72, 253.

Li, G., Regunathan, S., Barrow, C. J., Eshraghi, J., Cooper, R., Reis, D. J. (1994) Agmatine: an endogenous clonidine-displacing substance in the brain [see comments]. Science 263(5149): 966–969.

M. Max (1991) *Neuropathic Pain Syndromes,* ADVANCES IN PAIN RESEARCH & THERAPY 18.

Pinthong, D., Wright, I. K., Hanmer, C., Millns, P., Mason, R., Kendall, D. A. , Wilson, V. G. (1995) Agmatine recognizes alpha 2-adrenoceptor binding sites but neither activates or inhibits alpha 2-adrenoceptors. 351(1): 10–16.

T. Vanderah et al. (1996) *Single Intrathecal Injections of Dynorphin A or des-Tyr-dynorphins Produce Long-Lasting Allodynia in Rats: Blockade by MK-801 but not Naloxone,* PAIN 68, 275.

Yamamoto T and Yaksh TL Studies on the spinal interaction of morphine and the NMDA antagonist MK-801 on the hyperesthesia observed in a rat model of sciatic mononeuropathy. Neuroscience Letters January 1992 20; 135(1):67–70.

Yang, C Y, Wong, C S, Chang, J Y. Intrathecal ketamine reduces morphine requirements in patients with terminal cancer pain. Canadian Journal of Anaesthesia April 1996; 43(4):379–83.

Yang, X. C. , Reis, D. L. (1997) Agmatine selectively blocks the NMDA subclass of glutamate receptor channels in cultured mouse hippocampal neurons. Soc. Neurosci. Abstracts 23(2): 1763.

BRIEF SUMMARY OF THE INVENTION

The present invention is a method and composition of treating neuropathic pain by administering an effective amount of agmatine.

DETAILED DESCRIPTION OF THE PREFERRED EMBODIMENTS

Figure 1:
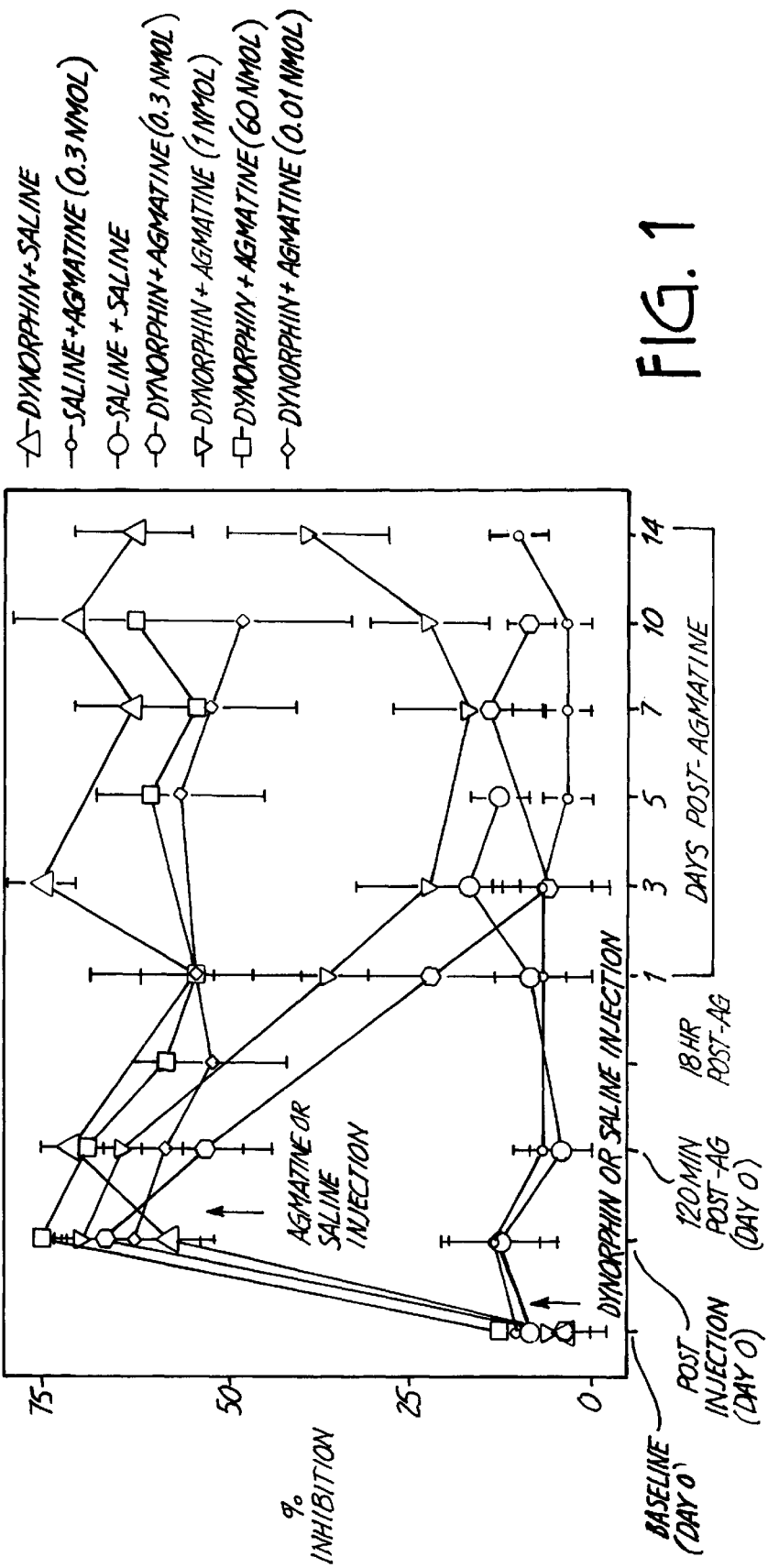
FIG. 1 is a graph demonstrating that agmatine induces dose-dependent rescue from permanent dynorphin-induced allodynia in mice.

The present invention is a method of treating neuropathic pain using agmatine. Agmatine is an endogenous amine that is produced by the enzymatic decarboxylation of the amino acid arginine.

It has been found that the administration of agmatine interacts with NMDA (Yang and Reis 1997), alpha-2-adrenergic (Pinthong), and imidazoline (Li et al. 1994) receptors in addition to different isoforms of nitric oxide synthase (Auguet et. al., 1995 and Galea et. al., 1996). It may be through one or a combination of these interactions that agmatine moderates and/or reverses plastic events in the central or peripheral nervous system, such as the spinal cord, that result in undesirable clinical sequelae, such as tolerance to opioids and neuropathic pain.

The administration of agmatine after neuropathic pain-inducing event thereby returns the patient to a non-pain, pre-injury state. It is also believed that the administration of agmatine prior to neuropathic pain-inducing event will avoid or substantially reduce the neuropathic pain experienced from the precipitating event.

Long-lasting allodynia (100 days) has been induced in mice by a single intrathecal injection of dynorphin A, an opioid peptide which is thought to induce neuropathic changes. (Laughlin et al, 1997.) The dynorphin-induced allodynia increases the sensitivity to non-noxious mechanical stimulation of the skin by application of von Frey filaments, which deliver a constant force when applied to their bending point. Use of von Frey filaments to measure sensitivity to mechanical stimuli or point pressure is a well-established technique in pain research. (See Beitel et al., 1976; Johansson et al., 1980; and LaMotte et al. 1986). Animals treated with dynorphin A respond to von Frey filaments of low force (0.4 mN); with a frequency of 60–80% by comparison, control mice respond with a frequency of 10% to the same force (0.4 mN) and same stimulation number. The difference between the dynorphin-treated and the control mice represents a hypersensitivity of the dynorphin-treated mice to that level of mechanical force. This hypersensitivity indicates an increased sensitivity to stimuli that are normally not noxious and is thought to be a measure of allodynia and to represent neuropathic pain.

Dynorphin A-treated mice that are administered agmatine one day after the chemical insult no longer respond to von Frey filament stimulation at the same level as dynorphin A-treated mice that did not receive agmatine post-treatment. The agmatine-treated mice respond comparably to saline-pretreated control mice.

Spinal administration of agmatine within a day of dynorphin-induced spinal injury rescues the spinal cord from development of dynorphin-induced allodynia. Intrathecal administration of agmatine also exhibits similar results when the injection is provided within 2–3 days of the dynorphin-induced spinal injury.

Agmatine administered according to the present invention at doses of up to 100 nanomoles is without analgesic effect and, in contrast to the analgesics, agmatine appears to rescue animals from their persistent pain state permanently because agmatine reduces sensitivity to the control levels throughout the study period of 24 days.

An advantage of administering agmatine according to the present invention as compared to the use of other NOS inhibitors and NMDA receptor antagonists is an apparent lack of side effects. For example other NOS inhibitors and NMDA receptor antagonists display spinal toxicity, including hindlimb paralysis and/or hyperlocomotion when evaluated using laboratory animals. Additionally, other non-competitive NMDA receptor antagonists, such as ketamine, that are being investigated for therapeutic application are thought to possess abuse potential. (Bratzke et al.1988, Corbett, 1989, and Dillman, 1995.)

Agmatine may be administered orally, sub-lingually, intranasally, buccally, parenterally, intrathecally, epidurally, topically, or rectally. Depending on the desired administration technique, agmatine may be formed into a suspension, a solution, or an emulsion in an aqueous or oily vehicle to assist in administering the agmatine. Agmatine may also be mixed with suspending agents, stabilizing agents, or dispersing agents.

Effective administration levels of agmatine will vary upon the state and circumstances of the patient being treated. As those skilled in the art will recognize, many factors that modify the action of an active ingredient will be taken into account by a treating physician such as the age, body weight, sex, diet and condition of the patient, the lapse of time between the injury and the administration of agmatine, and the administration technique. A person of ordinary skill in the art will be able to ascertain the optimal dosage for a given set of conditions in view of the experimental data contained herein.

We observe NMDA-antagonism behavior with an efficacy in mice with an ED50 of about 6.8 ug (30 nmol) of agmatine per mouse. Dalo and Larson (1990) observed NMDA-antagonism behavior in mice for ketamine with an ED60 of about 78 ng (0.3 nmol) of ketamine (an NMDA-receptor antagonist in clinical development) per mouse. We estimate the ED50 ratio for agmatine:ketamine in mice to be about 100:1 (agmatine is 100 times less potent) in this particular test of NMDA-induced nociception when given intrathecally. The intrathecal dose range where ketamine is active in humans is about 1 mg (3.6 uMol) (Yang et. al., 1996). Using the mouse intrathecal agmatine: ketamine potency ratio, we estimate NMDA-antagonism doses for agmatine for intrathecal administration to be about 82 mg (360 uMol) in humans.

The doses required to reverse agmatine-induced allodynia are approximately 100-fold lower than that used to antagonize the NMDA-induced behavior. Therefore we estimate the anti-allodynic doses for agmatine will be about 0.82 mg (3.6 uMol) in humans. We predict the effective intrathecal dose range for humans to be approximately 0.03–10 mg.

EXAMPLES 1–3

The following examples are presented to further describe the aspects of the present invention. The data presented in the examples demonstrate the effectiveness of agmatine in the alleviation of nociceptive (allodynic) behavior in mice distressed either chemically (by exposure to exogenous dynorphin, Example 1, Vanderah et. al., 1996; Laughlin, et. al. 1997) or mechanically (by ligation of the L5 spinal nerve, Kim and Chung 1992; Chung and Chung 1997). It is important to note that this ligation model is considered by many pain researchers to be the gold standard model of neuropathic pain in rodents. Example 3 represents a comparison between the abilities of higher doses agmatine to 1) acutely inhibit mechanical allodynia induced by L5 ligation, and 2) acutely inhibit nociceptive behaviors (biting) induced by intrathecal administration of 0.3 nmol of the excitatory amino acid analog N-methyl-D-aspartate (NMDA). These examples are not intended to limit the scope of the present invention.

Induction of Allodynia

Agmatine was tested for possible reversal of allodynia induced by one of two methods: dynorphin-induced allodynia and L5 spinal nerve ligation-induced allodynia. All experimental subjects were 15–25 g male ICR mice (Harlan, Madison, Wis.). All mice were housed in groups of ten in temperature- and humidity-controlled environments for four-five days before experimentation. All animals were maintained on a 12 hr light/dark cycle and had free access to food and water. Each animal was used only once. Baseline measurements (Day 0) were taken on all subjects prior to dynorphin injection or L5 spinal nerve ligation. To induce allodynia by chemical manipulation. dynorphin was injected intrathecally (3 nmol, i.t., Laughlin et. al., 1997). To induce allodynia by mechanical manipulation, the L5 spinal nerves were ligated according to the method of Kim and Chung, 1992, as modified for mice by Chung and Chung, 1997. Briefly described, under deep halothane (2–3%) anesthesia, the left paraspinal muscle of a mouse was separated from the spinous processes at the L4–S2 levels and removed. At this stage, the L6 transverse process and the rostral tip of the sacrum were visible. The L6 transverse process was then be removed to identify the L4–L6 spinal nerves visually. The L5 spinal nerves was tightly tied (ligated) with 6-0 silk thread. After hemostasis was confirmed, the wound was sutured with 3-0 silk thread and the skin closed with sterile wound clips. The animal was then placed in a moderately heated oxygen-enriched plastic enclosure to facilitate recovery. The animals were fully mobile within thirty minutes of cessation of anesthetic. As a control, in a separate group of animals, a sham surgery identical to the above was performed. The only difference with the sham operated animals was that their L5 spinal nerves were not ligated.

Figure 2:
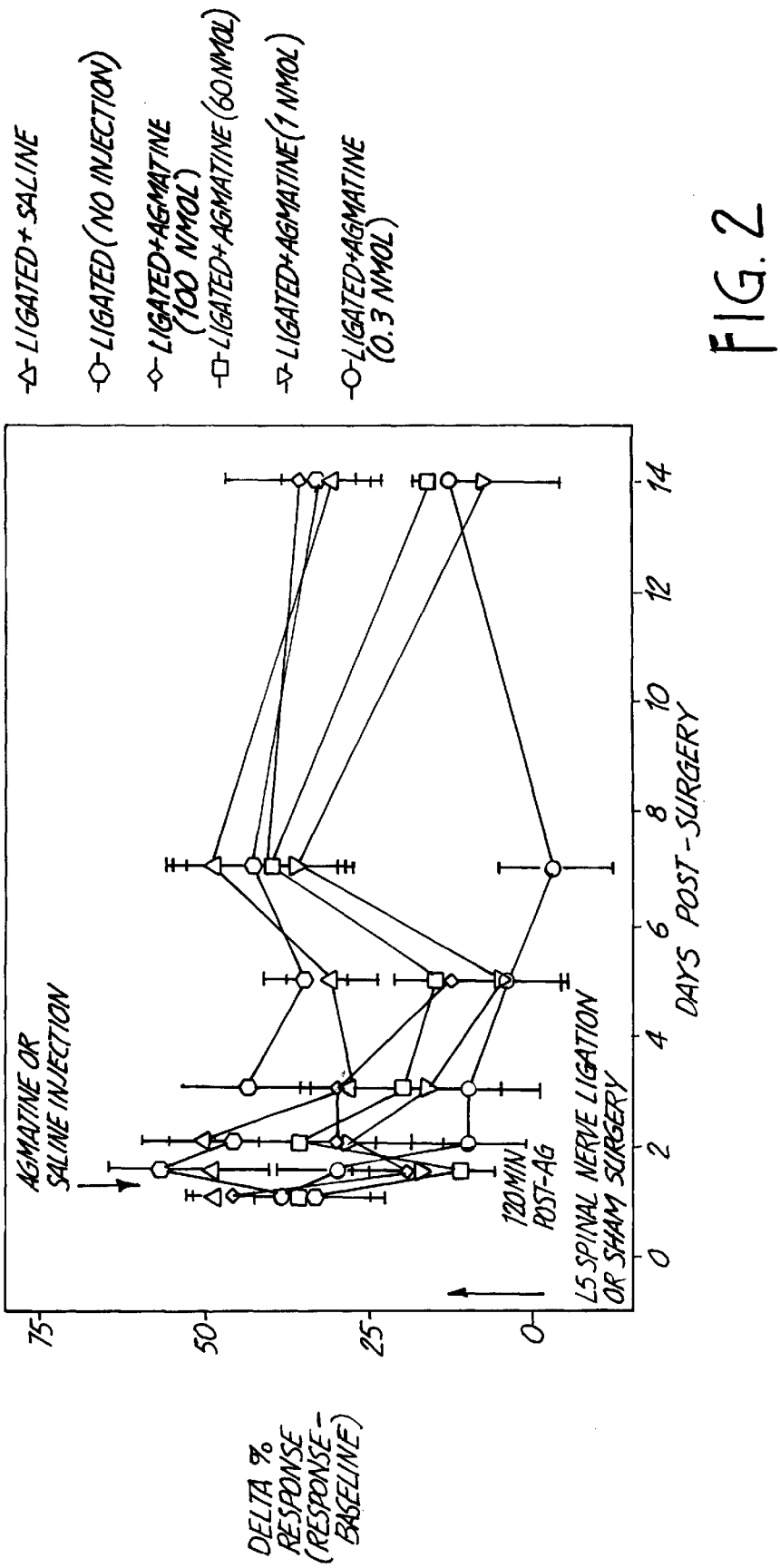
FIG. 2 is a graph demonstrating that agmatine induces dose-dependent rescue from permanent L5 ligation-induced allodynia in mice.

Experimental Design
(FIGS. 1, 2)

Allodynia to mechanical stimulation by von Frey (vF) monofilament application (to the bending point) was evaluated in the dynorphin-induced allodynia experiments according to the method described by Laughlin et. al., 1997. During each testing period, force (0.4 mN) was administered by applying the vF filament to the point of bending 3 times to the dorsal side each hindpaw. The data were pooled for a total of 6 stimulations per animal per time point. The data were expressed as a percent response of the 6 stimulations ((# of foot withdrawals or foot shakes/6)*100).

Allodynia to mechanical stimulation by vF monofilament was evaluated in the L5 ligation-induced allodynia experiments mice separately for each hindpaw. During each testing period, force (0.4 mN) was administered 5 times to the ventral side of each hindpaw in two separate trials for a total of 10 stimulations per test period. Baseline measurements demonstrated no difference between left (L) and right (R) paws (n=111 mice; L: 15% (s.e.m.: 1.3) R: 17% (s.e.m.: 1.3) p>0.05). Following unilateral nerve ligation, a significant difference was observed between left and right hindpaws (n=75, L: 55% (s.e.m. 2.1) R: 33% (s.e.m.: 2.6) p<0.05). The left paw represents the paw ipsilateral to the injured nerve and demonstrates increased sensitivity relative to that of the right paw, which is contralateral to the site of injury. The data are expressed as the delta percent response of the 10 stimulations (% Response at each specified time point D % Response of the Baseline). Following sham surgery, no significant difference was observed between left and right hindpaws (n=23, L: 27% (s.e.m. 4.8); R: 20% (s.e.m.: 3.1) p>0.05). Naive animals (receiving the same amount of stimulation at the same time points) demonstrate comparable responses between left and right paws (n=13, L: 5.4% (s.e.m. 2.4); R: 12% (s.e.m.: 3.2) p>0.05). Collectively these results indicate that the increased sensitivity of the paw ipsilateral to the ligation is specifically due to the specific mechanical distress imposed by the nerve ligation.

On the day following dynorphin injection or L5 ligation, allodynia was assessed as described above. Agmatine (0.1, 0.3, 1, 3, 4, 10, 30, 40, 60, 100, nmol, i.t.) or saline was subsequently administered as a single i.t. injection. The following experimental and control groups were included in most of the experiments:

Naive (no injection) required to determine the baseline response over repeated stimulations.
Naive+Agmatine required as a control for changes induced by agmatine on normal subjects.
Saline or Sham+Saline required as a control for changes induced by stress of the intrathecal injection.
Saline or Sham+Agmatine required as a control for changes induced by agmatine in saline-injected subjects.
Dynorphin or L5+ Saline required to see if the chemical or mechanical manipulation was effective in inducing mechanical allodynia.
Dynorphin or L5+ Agmatine. The experimental group demonstrates whether the compound was effective in rescuing the subject from dynorphin-induced allodynia.

After injection of agmatine or saline, multiple measurements were taken at 120 minutes post-agmatine injection, and then on days 2, 3 5, 7, 10, 14, 21, 24 and 28 post-agmatine (dynorphin-induced allodynia model) or post-surgery (L5 ligation-induced allodynia model). Each experiment was repeated and conducted at least once blinded.

Figure 3A:
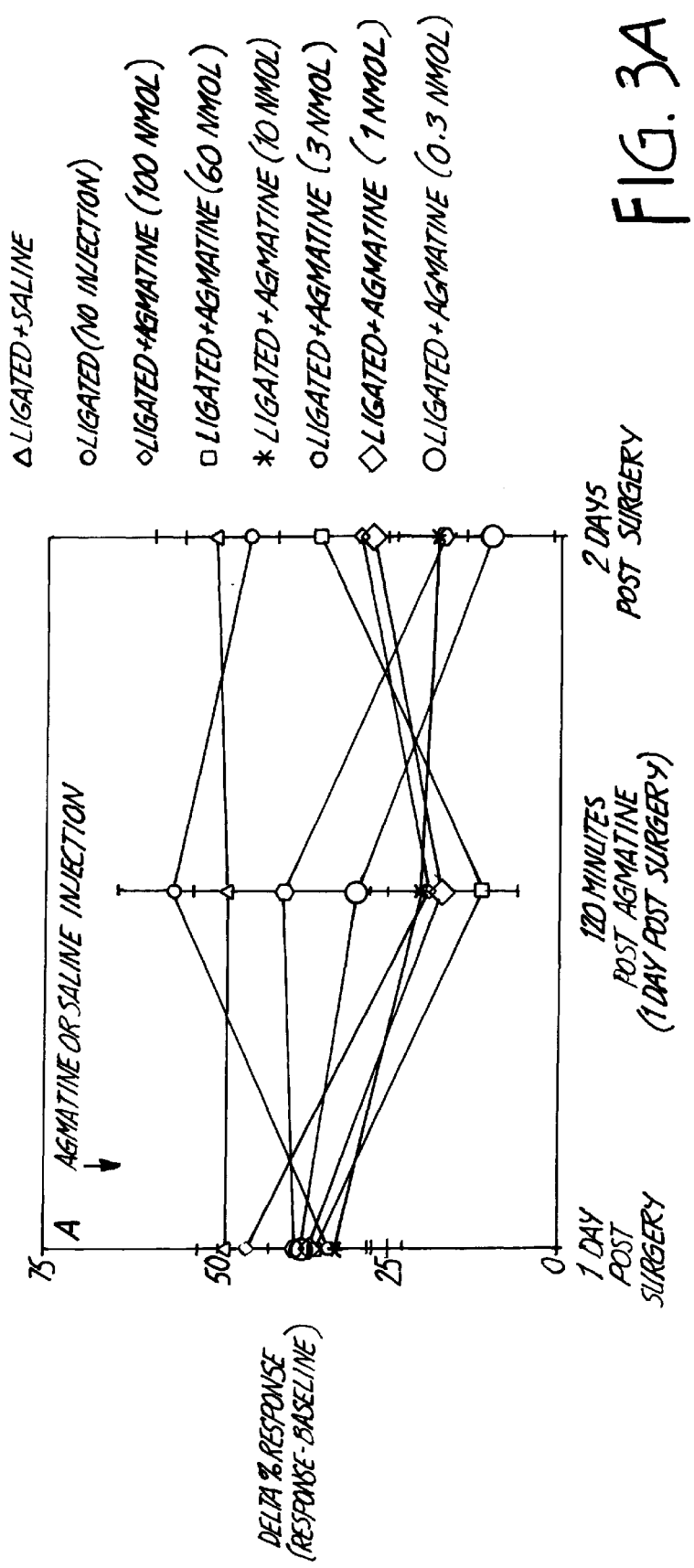
FIG. 3A is a graph of various treatment modes for rescue from permanent L5-ligation-induced allodynia in mice at 2 hours post agmatine treatment.
Figure 3B:
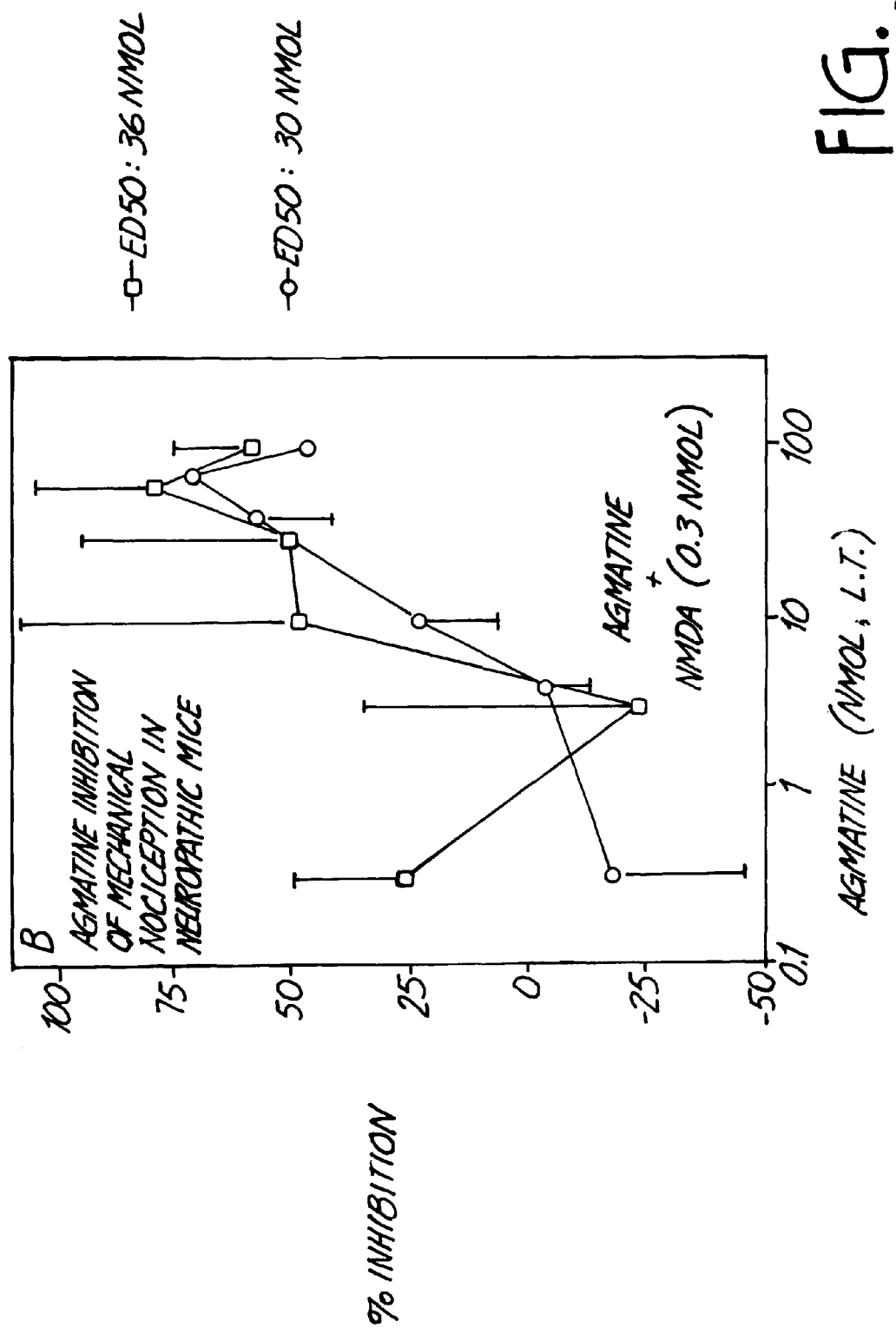
FIG. 3B is a graph of agmatine inhibition of NMDA-induced behavior.

Agmatine Inhibition of Mechanical Nociception in Neuropathic (L5 ligated) Mice.
(FIGS. 3A, 3B)

Intrathecal administration of agmatine produced a dose-related inhibition of mechanical allodynia measured 120 minutes post injection (FIG. 2). These data were analyzed for dose-dependency and expressed as a percent inhibition of the allodynic peak (percent response 1 day post-surgery). Each mouse served as its own control and % inhibition was determined using to the following equation:

(Delta % Response Day 1 Post-surgery D Delta % Response 120 Min Post-agmatine)

Delta % Response Day 1 Post-surgery

The ED50 value and confidence limits were calculated according to the method of Talarida and Murray (1987). Groups of 6 to 8 animals were used for each dose and/or each pretreatment.

Experimental Design for the NMDA Nociceptive Assay
(FIG. 3B)

Intrathecal administration of N-methyl-D-aspartate (NMDA) produces dose-related biting and scratching behavior in mice (Aanonsen and Wilcox, 1987). A constant dose of NMDA (0.3 nmol) was injected intrathecally and the number of NMDA-induced behaviors was counted for 1 minute. This dose of NMDA typically produces approximately 40–60 behaviors (scratches and bites directed to the hindlimbs and tail) during this post-injection minute. To determine the ability and potency of agmatine to block NMDA receptors, agmatine was co-administered (0.3, 4, 10, 40, 70 and 100 nmol, i.t.) with NMDA and the degree of agmatine-induced inhibition of NMDA-induced behavior evaluated. Percent inhibition was expressed as a percent change in the mean response of the control group (n=12 mice, mean=56 behaviors, s.e.m.=5.1) according to the following equation: % Inhibition=100*(56 D experimental value)/56; 56 was the number of behaviors observed in the control group of mice given 0.3 nmol NMDA i.t. The ED50 value and confidence limits were calculated according to the method of Tallarida and Murray (1987). Groups of 6 to 8 animals were used for each dose and/or each pretreatment.

RESULTS

Agmatine Dose-dependent Inhibition of Dynorphin-induced Allodynia

FIG. 1

A single spinal post-treatment with agmatine returned abnormal (sensitized) nociceptive responses of allodynic mice (mice in a chronic pain state) to normal levels. It is important to note that this hypersensitive state has been reported to persist out to 63 days (Laughlin et. al., 1997) and has been observed to persist as long as 100 days post-treatment (Laughlin. unpublished observations). FIG. 1 depicts the induction in mice of an apparently permanent allodynic (hyperresponsive to non-noxious, cutaneous stimuli) state after an intrathecal injection of a high dose of the peptide dynorphin A (1–17) (open upward triangles). A single intrathecal injection of agmatine one day after the injection of dynorphin fully (downward closed triangles: 0.3 nmol) or partially (downward open triangles: 1 nmol) reverts the animals behavior to normal levels (closed circles: saline+ saline injection). A single intrathecal injection of agmatine alone one day after the injection of saline had no effect (open circles: saline+0.3 nmol agmatine) relative to saline alone. Injection of high (open squares: 60 nmol) or low (open diamonds: 0.01 nmol) doses of agmatine are ineffective in reversing dynorphin-induced allodynia. This result suggests that agmatine may restore normal sensation to subjects experiencing neuropathic pain if it is administered at an appropriate dose at an appropriate time after the pain-initiating event or events. This experiment has been replicated.

Agmatine Dose-dependent Inhibition of L5 Ligation-induced Allodynia.

FIG. 2

Consistent with the results observed in FIG. 1, a single spinal post-treatment with agmatine in another neuropathic pain model returns sensitized nociceptive responses of allodynic mice to normal levels. The graph depicts the induction in mice of a persistent allodynic state after L5 spinal nerve ligation (Ligated+Saline: open upright triangles, Ligated (no injection): closed upright triangles). Following agmatine (0.3, 1, 3, 10, 30, 60, 100 nmol, i.t.) administration, responsivity of the affected hindpaw of the ligated animals dose-dependently decreased at 2 hours post-agmatine administration (11)50: 36 nmol FIG. 3A, B). By post-surgery day 2, those subjects that received doses of agmatine (3, 10, 30, 60, 100 nmol) that effectively decreased responsivity at 2 hours post-drug treatment, demonstrated a return to allodynic levels of responding. For the most part, responsivity in those groups remained comparable to the allodynic control groups (Ligated+ Saline: open upright triangles; Ligated (no injection): closed upright triangles) throughout the remainder of the testing period (days 3–14). In other words, 3 or more nmol agmatine produced acute but not chronic remission of the hyperresponsive state. By day 2, certain groups of subjects that had received doses of agmatine (downward closed triangles: 0.3 nmol; downward open triangles: 1 nmol) that did not significantly affect responsivity at 2 hours post-drug treatment, demonstrated a return to normal levels of responding by day 3. Responsivity in those groups largely remained comparable to the normal control groups (naive or sham+saline, data not shown) throughout the testing period. In other words, 0.3 and 1 nmol agmatine produced chronic but not acute remission of the hyperresponsive state. Naive or sham controls (agmatine-treated or saline-treated) did not demonstrate a substantial increase in responsivity on either paw throughout the testing period (days 1–14, data not shown). Injection of high (open squares: 60 nmol; open diamond: 100 nmol) doses of agmatine was less effective than the more moderate doses in reversing L5 spinal nerve ligation-induced allodynia.

FIGS. 3A and 3B

High doses of agmatine (10–100 nmol, i.t.) antagonize NMDA receptor activation

Figure A

FIG. 3A is an expanded representation of the 120 minute post-agmatine time point in FIG. 2; downward deflections represent agmatine-induced, dose-dependent inhibition of allodynia. Higher doses of agmatine are generally more efficacious than lower doses.

Figure B

Agmatine-induced dose-dependent inhibition of the allodynia graphed in part A yields a dose-inhibition curve (closed circles, $ED_{50}$ value: 36 nmol). This dose-inhibition curve is compared to agmatine-induced inhibition of behavior elicited by a constant dose of intrathecally administered NMDA (open circles, $ED_{50}$ value: 30 nmol). These data show that the intrathecal doses of agmatine (10–100 nmol, i.t.) that acutely attenuate (but do not chronically rescue mice from (FIG. 1, 2)) allodynia are the same doses that inhibit NMDA-induced behavior. We interpret this result to indicate that agmatine-induced antagonism of NMDA receptors in mouse spinal cord mediates acute and temporary relief of allodynic hyperresponsivity. By contrast, the dose of agmatine that proved effective in chronically relieving allodynia in both neuropathic pain models (FIG. 1, 2: 0.3 nmol) showed minimal acute attenuation of allodynia and no inhibition of NMDA-induced behavior. We interpret these results to mean that agmatine may not act via NMDA antagonism to exert its anti-allodynic effect and instead acts at other, as yet to be determined, binding sites to exert this therapeutic action.

Agmatine Modulation Nociception in other Tests

We have observed that spinally-administered agmatine (0.3–100 nmol, i.t.) does not produce antinociception (analgesia) in tail flick, mechanical nociception (vF stimulation in naive mice), or the substance P test (data not shown). Others have shown that systemically administered agmatine does not produce antinociception in the tail flick test (Kolesnikov and Pasternak, 1996). Systemically administered agmatine has also been tested for its potential effect on spinal nociceptive reflexes evoked by mechanical and electrical stimuli. (Bradley K J and Headley P M, 1997) Agmatine did not affect reflexes until very high doses (200 mg/kg i.v.) in the range where it produced adverse cardiovascular disturbances. These electrophysiological results agree with the above behavioral results and support the general observation that agmatine is not, in and of itself, analgesic. Results from this laboratory (Fairbanks and Wilcox, 1997) further distinguish agmatine from NMDA receptor antagonists: co-administration of agmatine with morphine i.t. fails to potentiate morphine analgesia; NMDA antagonists have been observed potentiate morphine (Yamamoto T and Yaksh T L, 1992).

Conclusion

The effect of agmatine to reduce sensitivity in allodynic mice, therefore, appears to be specific to that indication and this selectivity distinguishes agmatine from currently used analgesics. At doses greater than 10 nmol i.t. (or 30 mg/kg i.p. (intraperitoneal) or 100 mg/kg p.o. (per os)) agmatine is capable, however, of inhibiting scratching behavior induced by intrathecal injection of NMDA. Doses lower than 1 nmol i.t. (or 3 mg/kg i.p. or 10 mg/kg p.o.) do not inhibit this behavior in rodents. Therefore, at the higher doses agmatine acts as an antagonist at the NMDA receptor. These doses are ineffective for long term relief of dynorphin or L5-ligation induced allodynia. Lower doses that are ineffective for antagonizing the NMDA-induced behavior are effective for reversing allodynia induced by L5k-ligation or intrathecal administration of dynorphin. Taken together, these results indicate that agmatine exerts its anti-allodynic effect through different (as yet undefined) mechanisms from NMDA receptor antagonism.

What is claimed is:

1. A method for treating neuropathic pain, the method comprising administering an effective amount of agmatine to an individual in need thereof.

2. The method of claim 1 wherein the agmatine is administered intrathecally.

3. The method of claim 1 wherein the agmatine is administrated in a dosage range of approximately 0.03–10 mg.

4. The method of claim 3 wherein the agmatine is administrated in an approximate dose of 0.82 mg.

5. The method of claim 1 wherein the agmatine is formed into a suspension, a solution, or an emulsion prior to administration.

6. The method of claim 1 wherein the agmatine is mixed with suspending agents, stabilizing agents, dispersing agents, or combinations thereof prior to administration.

* * * * *